(12) United States Patent
Dante et al.

(10) Patent No.: US 10,592,745 B2
(45) Date of Patent: Mar. 17, 2020

(54) ON-LINE OIL AND FOREIGN MATTER DETECTION SYSTEM AND METHOD EMPLOYING HYPERSPECTRAL IMAGING

(71) Applicant: ALTRIA CLIENT SERVICES LLC, Richmond, VA (US)

(72) Inventors: Henry M. Dante, Midlothian, VA (US); Samuel Timothy Henry, Midlothian, VA (US); Seetharama C. Deevi, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 15/857,322

(22) Filed: Dec. 28, 2017

(65) Prior Publication Data

US 2018/0121706 A1 May 3, 2018

Related U.S. Application Data

(63) Continuation of application No. 14/443,990, filed as application No. PCT/US2013/070812 on Nov. 19, 2013, now Pat. No. 9,886,631.

(Continued)

(51) Int. Cl.
*A24B 15/18* (2006.01)
*G01N 21/31* (2006.01)
(Continued)

(52) U.S. Cl.
CPC ............. *G06K 9/0063* (2013.01); *A24B 3/16* (2013.01); *A24B 15/18* (2013.01); *B07C 5/342* (2013.01);
(Continued)

(58) Field of Classification Search
CPC ...... B07C 5/342; B07C 5/366; G06K 9/0063; G06K 9/4605; G06K 9/6202; A24B 3/16; A24B 15/18; G01J 3/28; G01J 3/2823
(Continued)

(56) References Cited

U.S. PATENT DOCUMENTS

| 3,854,586 A | 12/1974 | Perkins, III |
| 3,939,983 A | 2/1976 | Asfour |

(Continued)

FOREIGN PATENT DOCUMENTS

| CN | 101627832 A | 1/2010 |
| WO | 00/58035 A1 | 10/2000 |

(Continued)

OTHER PUBLICATIONS

International Search Report and Written Opinion of the International Searching Authority issued in PCT/IB2010/053952, dated Dec. 22, 2010.

(Continued)

*Primary Examiner* — Terrell H Matthews
(74) *Attorney, Agent, or Firm* — Harness, Dickey & Pierce, P.L.C.

(57) ABSTRACT

A method for removing foreign matter from an agricultural product stream of a manufacturing process. The method includes conveying a product stream past an inspection station; scanning a region of the agricultural product stream as it passes the inspection station using at least one light source of a single or different wavelengths; generating hyperspectral images from the scanned region; determining a spectral fingerprint for the agricultural product stream from the hyperspectral images; comparing the spectral fingerprint obtained in step (c) to a spectral fingerprint database containing a plurality of fingerprints using a computer processor to determine whether foreign matter is present (Continued)

and, if present, generating a signal in response thereto; and removing a portion of the conveyed product stream in response to the signal. A system for detecting foreign matter within an agricultural product stream is also provided.

23 Claims, 5 Drawing Sheets

Related U.S. Application Data

(60) Provisional application No. 61/728,123, filed on Nov. 19, 2012.

(51) Int. Cl.
| | |
|---|---|
| *B07C 5/342* | (2006.01) |
| *B07C 5/36* | (2006.01) |
| *G01N 21/84* | (2006.01) |
| *G06K 9/00* | (2006.01) |
| *G01J 3/28* | (2006.01) |
| *G06K 9/62* | (2006.01) |
| *G06K 9/46* | (2006.01) |
| *G06F 16/51* | (2019.01) |
| *A24B 3/16* | (2006.01) |
| *G06T 7/00* | (2017.01) |

(52) U.S. Cl.
CPC ............... *B07C 5/366* (2013.01); *G01J 3/28* (2013.01); *G01J 3/2823* (2013.01); *G01N 21/31* (2013.01); *G01N 21/84* (2013.01); *G06F 16/51* (2019.01); *G06K 9/4604* (2013.01); *G06K 9/6202* (2013.01); *G06T 7/0008* (2013.01); *H05K 999/99* (2013.01); *G01J 2003/2826* (2013.01); *G01N 2021/8461* (2013.01); *G01N 2021/8466* (2013.01); *G06K 2009/4657* (2013.01); *G06T 2207/20024* (2013.01); *G06T 2207/30108* (2013.01); *G06T 2207/30188* (2013.01)

(58) Field of Classification Search
USPC .......................................... 209/576, 577, 552
See application file for complete search history.

(56) References Cited

U.S. PATENT DOCUMENTS

| | | | |
|---|---|---|---|
| 4,018,674 A | 4/1977 | Morris | |
| 4,528,993 A | 7/1985 | Sensabaugh et al. | |
| 4,609,108 A | 9/1986 | Hristozov et al. | |
| 4,624,269 A | 11/1986 | Story et al. | |
| 4,778,987 A | 10/1988 | Saaski et al. | |
| 4,836,224 A | 6/1989 | Lawson et al. | |
| 4,924,883 A | 5/1990 | Perfetti et al. | |
| 4,924,888 A | 5/1990 | Perfetti et al. | |
| 4,987,907 A | 1/1991 | Townend | |
| 5,056,537 A | 10/1991 | Brown et al. | |
| 5,085,325 A | 2/1992 | Jones et al. | |
| 5,092,352 A | 3/1992 | Sprinkle | |
| 5,159,942 A | 11/1992 | Brinkley et al. | |
| 5,220,930 A | 6/1993 | Gentry | |
| 5,301,694 A | 4/1994 | Raymond et al. | |
| 5,360,023 A | 11/1994 | Blakley et al. | |
| 5,360,024 A | 11/1994 | Greig | |
| 5,387,416 A | 2/1995 | White | |
| 5,476,108 A | 12/1995 | Dominguez et al. | |
| 5,972,404 A | 10/1999 | van Lengerich | |
| 6,400,833 B1 | 6/2002 | Richert | |
| 6,421,126 B1 | 7/2002 | Kida et al. | |
| 6,504,943 B1 | 1/2003 | Sweatt et al. | |
| 6,587,575 B1 * | 7/2003 | Windham ............... G01N 21/31 |
| | | | 250/458.1 |
| 6,646,264 B1 | 11/2003 | Modiano et al. | |
| 6,701,936 B2 | 3/2004 | Shafer et al. | |
| 6,730,832 B1 | 5/2004 | Dominguez et al. | |
| 6,819,798 B2 * | 11/2004 | Gorin ..................... G01J 3/2823 |
| | | | 250/316.1 |
| 6,953,040 B2 | 10/2005 | Atchley et al. | |
| 7,032,601 B2 | 4/2006 | Atchley et al. | |
| 7,142,988 B1 | 11/2006 | Johnson | |
| 7,335,847 B2 | 2/2008 | Drewes et al. | |
| 7,383,840 B2 | 6/2008 | Coleman | |
| 7,411,682 B2 | 8/2008 | Moshe | |
| 7,450,761 B2 * | 11/2008 | Portigal ............... G06K 9/0063 |
| | | | 382/103 |
| 7,518,710 B2 | 4/2009 | Gao et al. | |
| 8,564,769 B2 * | 10/2013 | Zou ..................... G06F 3/005 |
| | | | 356/300 |
| 8,775,219 B2 * | 7/2014 | Swanson ................ G06Q 50/16 |
| | | | 705/4 |
| 8,953,158 B2 * | 2/2015 | Moshe .................. B07C 5/3422 |
| | | | 356/300 |
| 8,967,851 B1 | 3/2015 | Kemeny | |
| 9,870,505 B2 * | 1/2018 | Dante ..................... A24B 3/16 |
| 2001/0000386 A1 | 4/2001 | Peele | |
| 2002/0008055 A1 | 1/2002 | Campbell et al. | |
| 2003/0075193 A1 | 4/2003 | Li et al. | |
| 2003/0131859 A1 | 7/2003 | Li et al. | |
| 2004/0084056 A1 | 5/2004 | Lawson et al. | |
| 2004/0255965 A1 | 12/2004 | Peifetti et al. | |
| 2005/0057263 A1 | 3/2005 | Moshe et al. | |
| 2005/0066984 A1 | 3/2005 | Crooks et al. | |
| 2005/0066986 A1 | 3/2005 | Nestor et al. | |
| 2005/0244521 A1 | 11/2005 | Strickland et al. | |
| 2006/0292246 A1 * | 12/2006 | Wu ..................... G01N 30/8675 |
| | | | 424/725 |
| 2008/0245377 A1 | 10/2008 | Marshall et al. | |
| 2009/0171591 A1 | 7/2009 | Timmis et al. | |
| 2009/0293889 A1 | 12/2009 | Kumar et al. | |
| 2011/0125477 A1 | 5/2011 | Lightner et al. | |
| 2012/0250025 A1 * | 10/2012 | Moshe .................. B07C 5/3422 |
| | | | 356/451 |
| 2012/0257047 A1 | 10/2012 | Biesemans et al. | |
| 2012/0321759 A1 * | 12/2012 | Marinkovich ....... A61B 5/0531 |
| | | | 426/231 |
| 2013/0022250 A1 * | 1/2013 | Nygaard ................. A61J 3/007 |
| | | | 382/128 |
| 2015/0044098 A1 * | 2/2015 | Smart .................. A61B 5/0013 |
| | | | 422/82.05 |
| 2015/0224544 A1 * | 8/2015 | McGloughlin ......... B07C 5/342 |
| | | | 209/577 |
| 2015/0283586 A1 * | 10/2015 | Dante ..................... A24B 3/16 |
| | | | 209/577 |
| 2017/0348900 A1 * | 12/2017 | Williams ............ G03F 7/70416 |

FOREIGN PATENT DOCUMENTS

| | | | | |
|---|---|---|---|---|
| WO | 02/37990 A2 | 5/2002 | | |
| WO | 2004/095959 A1 | 11/2004 | | |
| WO | 2005/016036 A1 | 2/2005 | | |
| WO | 2005/041699 A2 | 5/2005 | | |
| WO | 2005/063060 A1 | 7/2005 | | |
| WO | 2007041755 A1 | 4/2007 | | |
| WO | WO -2007041755 A1 * | 4/2007 | ............. B07C 5/342 |
| WO | 2007/0999540 A2 | 9/2007 | | |
| WO | 2011/027315 A1 | 3/2011 | | |
| WO | 2014/078858 A1 | 5/2014 | | |
| WO | 2014/078861 A1 | 5/2014 | | |
| WO | 2014/078862 A1 | 5/2014 | | |

OTHER PUBLICATIONS

United States Final Office Action for U.S. Appl. No. 14/443,995, dated Jul. 26, 2018.
United States Office Action for corresponding U.S. Appl. No. 15/846,706 dated Apr. 9, 2019.
United States Office Action for corresponding U.S. Appl. No. 14/443,995 dated May 22, 2019.
International Preliminary Report on Patentability of PCT/IB2010/053952 dated Mar. 6, 2012.

(56) References Cited

OTHER PUBLICATIONS

International Preliminary Report on Patentability of PCT/US2013/070809 dated May 19, 2015.
International Preliminary Report on Patentability of PCT/US2013/070812 dated May 19, 2015.
International Preliminary Report on Patentability of PCT/US2013/070814 dated May 19, 2015.
International Search Report & Written Opinion of International Application No. PCT/IB2010/053952 dated Dec. 10, 2010.
International Search Report & Written Opinion of International Application No. PCT/US2013/070809 dated Mar. 7, 2014.
International Search Report & Written Opinion of International Application No. PCT/US2013/070812 dated Mar. 7, 2014.
International Search Report & Written Opinion of International Application No. PCT/US2013/070814 dated Mar. 7, 2014.
C.W. Bacon, et al.; "Biochemical Changes in Tobacco During Flue Curing", USDA Tech. Bulletin No. 1032 (1951).
C.W. Bacon, et al.; "Chemical Changes in Tobacco during Flue-Curing", Industrial & Engineering Chemistry, 44(2), 292-309 (1952).
D. W. Bombick, et al.; "Evaluation of the Genotoxic and Cytotoxic Potential of Mainstream Whole Smoke and Smoke Condensate from a Cigarette Containing a Novel Carbon Filter, "Fundamental and Applied Toxicology, vol. 39, pp. 11-17 (1997).
O.A. Brown, et al; "Engineering Phases of Curing Bright Leaf Tobacco", Agriculture Engineering, 29(3), 109-111 (1948).
Colin L. Browne; "The Design of Cigarettes", 3.sup.rd Ed., pp. 43 (Sep. 1990); http://legacy.library.ucsf.edu/tid/fxb76b00.pdf.
Albert H. Cooper, et al; "Drying and Curing of Bright Leaf Tobacco by Means of Conditioned Air: Enginering Experiment Station Series" Bulletin of The Virginia Polytechnic Institute, 37(6), 3-28 (1939).
F.R. Darkis, et al; "FLUE-CURED TOBACCO Correlation between Chemical Composition and Stalk Position of Tobaccos Produced under Varying Weather Conditions", Industrial & Engineering Chemistry, 28 (10), pp. 1214-1223 (1936).
F.R. Darkis, et al; "Cigarette Tobaccos. Chemical Changed that Occur during Processing" Industrial & Engineering Chemistry, 44 (2), 284-291 (1952).
D. Layten Davis, et al; "Tobacco: Production, Chemistry and Technology", 1st Edition, (Jul. 1999), pp. 131-133, 346, and 440-451.
"Flue-Cured Tobacco Information", North Carolina Cooperative Extension Service, North Carolina State University, (1993).
Pilar Beatriz Garcia-Allende, et al; "Hyperspectral Imaging Sustains Production-Process Competitiveness", Spie Newsroom, (Jan. 1, 2010), DOI:10.11172.1201003.002681.
Pilar Beatriz Garcia-Allende, et al; "Hyperspectral Imaging for Diagnosis and Quality Control in Agri-food and Industrial Sectors, Proceedings of SPIE", vol. 7726, (Apr. 30, 2011), ISSN: 0277-786X, DOI: 101117.12.744506.
W.W. Garner; "Principles and Practical Methods of Curing Tobacco", USDA Bulletin No. 143, 7-54 (1909).
Robin Gruna, et al; "Hyperspectral Imaging - From Laboratory to In-line Food Sorting", Cigar Workshop on Image Analysis in Agriculture, (Jan. 1, 2010).
S. N. Hawks, Jr.; "Principles of Flue-Cured Tobacco Production", Second Edition (1978).
William H. Johnson, et al; "Bulk Curing of Bright Leaf Tobacco", Tobacco Science, 4, pgs. 49-55 (1960).
William H. Johnson; "Production factors affecting chemical properties of the flue-cured leaf", Tobacco International 177(11): pp. 12-19 (1975).
Timothy Kelman, et al; "Classification of Chinese Tea Samples for Food Quality Control Using Hyperspectral Imaging", Hyperspectral Imaging Conference, (Jan. 1, 2011).
Paul D. Legg, et al; 40th Tobacco Chemists' Research Conference; (Oct. 13-16, 1986); Conference Papers—"Nitrogenous Constituents in Dark Air-Cured and Fire-Cured Cultivars.".
Russ Ouellette; "The Basics of Tobacco and Blending", pipesmagaazine.com, (Jul. 14, 2010) Retrieved from the Internet: URL: http://pipesmagazine.com/blog/put-that-in-your-pipe/the-basucs-of-tobacco-blending.
David M. Peele, et al; "Chemical and Biochemical Changes During the Flue-Curing of Tobacco"; Recent Advances in Tobacco Science, Impact of Plant Manipulation and Post Harvest Phenomena on Leaf Composition, vol. 21, pp. 81-123 (Sep. 1995).
Luis Rodriguez-Cobo, et al; "Raw Material Classification by Means of Hyperspectral Imaging and Hierarchical Temporal Memories", IEEE Sensors Journal, IEEE Service Center, New York, NY, US, vol. 12, No. 9, (Sep. 1, 2012), ISSN:1530-437X, DOI: 10.1109.2012.2202898.
C.W. Suggs, et al; "Bulk Density and Drying Effect on Air Flow Through Flue-Cured Tobacco Leaves", Tobacco Science yearbook, 33, pp. 86-90 (1989).
Ernst Voges; "Tobacco Encyclopedia", Tobacco Journal International, pp. 44-45 (1984).
E. K. Walker, et al; "Curing Flue-Cured Tobacco in Canada", Agriculture Canada, Publication 1312/E (1987).
United States Office Action for U.S. Appl. No. 15/846,706, dated Oct. 1, 2019.
United States Office Action for U.S. Appl. No. 14/443,995, dated Nov. 29, 2019.
United States Notice of Allowance for U.S. Appl. No. 15/846,706, dated Jan. 15, 2020.

* cited by examiner

ON-LINE OIL AND FOREIGN MATTER DETECTION SYSTEM AND METHOD EMPLOYING HYPERSPECTRAL IMAGING

RELATED APPLICATIONS

This application is a continuation of U.S. Ser. No. 14/443,990, filed May 19, 2015, allowed, which is a National Stage Entry of PCT/US2013/070812, filed Nov. 19, 2013, which claims priority to U.S. Ser. No. 61/728,123, filed Nov. 19, 2012, the contents of each are hereby incorporated by reference herein in their entireties.

FIELD

Disclosed herein is an on-line system and method for the detection and separation of unwanted materials and/or foreign matter, using hyperspectral imaging and analysis.

ENVIRONMENT

Tobacco delivered for processing into filler for cigarettes may occasionally contain foreign matter such as pieces of the container in which it is shipped and/or stored, bits of string and paper, and other items. There remains a need for methods and systems to remove foreign, non-tobacco related materials (NTRM or foreign material).

Another area where it is important to optically inspect and sort a moving stream of product is in the food-processing industry where there is a need to automatically sort food products by optical inspection of the food products to identify food articles having undesirable visual characteristics or intermixed foreign material. Examples include fruits, vegetables, baked products, nuts and the like. Other areas requiring a similar sorting of products or articles includes the sorting of naturally occurring products such as meat products, particularly of quartered or cubed poultry or beef products. In the processing and packaging of comestible consumer products and products designed to provide tobacco enjoyment, oils, greases and lubricants may come into contact with the product being produced.

In the case of products designed to provide tobacco enjoyment, tobacco leaf may be contacted by machinery during harvesting, curing and transport to a stemmery. When leaf is provided in strip form at a stemmery, and cut or otherwise shredded to the desired size, while unlikely, oils, greases and lubricants can come into contact with the tobacco. Likewise, lubricants used in operating the various machines used in the processing of the tobacco can come into contact with that tobacco. The sources of lubricant can vary, such as when a particular piece of machinery or component of that piece of machinery fails to operate in an optimum fashion.

Although extremely unlikely, lubricants may come into contact with tobacco due to leakage of lubricants through gaskets or seals, from sliding mechanisms, from drum systems, from gear boxes, from pumps, from sealed rolling bearing units, from chains and belts, and the like. Lubricants are used in conditioning cylinders, threshers, separators, redryers, receivers, feeders, conveyors, cutters, blenders, tobacco presses and other such pieces of equipment that are commonly used in tobacco stemmeries and in tobacco primary processing operations. Foreign matter may sometimes be introduced during harvesting, baling, transporting and bundling operations.

Since lubricants of similar compositions are used throughout the various stages of tobacco treatment and cigarette manufacture, it is often difficult for the cigarette manufacturer to locate the source of a particular lubricant. As such, the cigarette manufacturer is forced to conduct a time consuming search for the source of the lubricant, in order to identify and remove the material that may have come in contact with it.

As in the case of any agricultural product, tobacco may be characterized by a wide variety of physical, chemical, and/or biological properties, characteristics, features, and behavior, which are associated with various aspects relating to agriculture, agronomy, horticulture, botany, environment, geography, climate, and ecology of the tobacco crop and plants thereof from which tobacco leaves are derived, as well as the manner in which the tobacco has been processed, aged or fermented to produce the sensorial characteristics sought to be achieved by such further processing. Moreover, as those skilled in the art will plainly recognize, these characteristics can vary in time throughout further processing, aging or fermentation.

In the general technique of hyperspectral imaging, one or more objects in a scene or sample are affected in a way, such as excitation by incident electromagnetic radiation supplied by an external source of electromagnetic radiation upon the objects, which causes each object to reflect, scatter and/or emit electromagnetic radiation featuring a spectrum.

Hyperspectral imaging and analysis is a combined spectroscopy and imaging type of analytical method involving the sciences and technologies of spectroscopy and imaging. By definition, hyperspectral imaging and analysis is based on a combination of spectroscopy and imaging theories, which are exploitable for analyzing samples of physical, chemical, and/or biological matter in a highly unique, specialized, and sophisticated, manner.

Hyperspectral images generated by and collected from a sample of matter may be processed and analyzed by using automatic pattern recognition and/or classification type data and information processing and analysis, for identifying, characterizing, and/or classifying, the physical, chemical, and/or biological properties of the hyperspectrally imaged objects in the sample of matter.

None of the commercially available optical scanning and sorting systems can detect and reject product that has come in contact with oil or lubricant and/or other NTRM. As such, it would be advantageous if the inspection for oils, greases, lubricants, NTRM and other undesirable materials on or intermixed with consumer products, such as food, tobacco and tobacco products could be conducted on-line, that is, in real time, using an optical scanning and sorting system during the production process.

SUMMARY

Disclosed herein is a method for removing foreign matter (including oil or lubricant in product) from an agricultural product stream of a manufacturing process. The method includes conveying a product stream past an inspection station; scanning a region of the agricultural product stream as it passes the inspection station using at least one light source of a single or different wavelengths; generating hyperspectral images from the scanned region; determining a spectral fingerprint for the agricultural product stream from the hyperspectral images; comparing the spectral fingerprint so obtained to a spectral fingerprint database containing a plurality of fingerprints using a computer processor to determine whether foreign matter is present and, if present, generating a signal in response thereto; and removing a portion of the conveyed product stream in response to the signal.

In some forms, the method includes the step of causing the portion of the conveyed product stream to fall under the influence of gravity in a cascade.

In some forms, the cascade is a turbulent cascade.

In some forms, the step of removing a portion of the conveyed agricultural product stream in response to the signal further includes directing fluid under pressure at the portion of the agricultural product stream.

In some forms, the fluid is a gas.

In some forms, the gas is pressurized air.

In some forms, the agricultural product is tobacco.

In some forms, the agricultural product is tea.

In some forms, the at least one light source is positioned to minimize the angle of incidence of each beam of light with the agricultural product stream.

In some forms, the at least one light source for providing a beam of light comprises a light source selected from the group consisting of a tungsten light source, a halogen light source, a xenon light source, a mercury light source, an ultraviolet light source, and combinations thereof.

In a further aspect, provided is a system for detecting foreign matter (including oil or lubricant in product) within an agricultural product stream. The system includes a first conveying means for delivering a product stream; an inspection station comprising (i) at least one light source of a single or different wavelengths for providing a beam of light to scan a region of the agricultural product stream as it passes the inspection station, and (ii) a hyperspectral camera system for providing a three dimensional hyperspectral image cube; a computer processor structured and arranged to determine a spectral fingerprint for the agricultural product stream from the hyperspectral image cube and to compare the spectral fingerprint obtained to a spectral fingerprint database containing a plurality of fingerprints to determine whether foreign matter is present and, if present, generating a signal in response thereto.

In some forms, the system includes at least one deflecting system responsive to the signals obtained from the computer processor, the at least one deflecting system directing fluid under pressure at a portion of the product stream when the computer processor determines that foreign matter is present in the product stream.

In some forms, the fluid so directed is effective to remove the foreign matter.

In some forms, the system includes a second conveying means located below and spaced vertically from the first conveying means for further conveying the product stream from the first conveying means, wherein the product stream is transferred from the first conveying means to the second conveying means by falling therebetween under the influence of gravity in a cascade.

In some forms, the cascade is a turbulent cascade.

In some forms, the first conveying means is an inclined vibrating conveyor.

In some forms, the fluid is a gas.

In some forms, the gas is air.

In some forms, the agricultural product is tobacco.

In some forms, the agricultural product is tea.

In some forms, the at least one light source is positioned to minimize the angle of incidence of each beam of light with the agricultural product stream.

In some forms, the at least one light source for providing a beam of light comprises a light source selected from the group consisting of a tungsten light source, a halogen light source, a xenon light source, a mercury light source, an ultraviolet light source, and combinations thereof.

In yet another aspect, disclosed herein is a method of creating a database for use in identifying foreign material (including oil or lubricant) agricultural product that may be present in a manufacturing process for producing an agricultural product. The method utilizes hyperspectral imaging and includes the steps of (a) obtaining a dark image and a reference image for calibration; (b) analyzing the reference image to obtain calibration coefficients; (c) obtaining a hyperspectral image for an agricultural sample; (d) removing dark values and normalizing the agricultural sample image; (e) applying calibration coefficients to compensate for fluctuations in system operating conditions; (f) repeating steps (c)-(e) for all agricultural samples; (g) obtaining a hyperspectral image for a foreign material sample; (h) removing dark values and normalizing the agricultural sample image; (i) applying calibration coefficients to compensate for fluctuations in system operating conditions; (j) repeating steps (g)-(i) for all samples and (k) storing all hyperspectral sample hypercubes to form the database.

In one form, the computer database is stored in a computer readable medium.

Certain forms disclosed herein are implemented by performing steps or procedures, and sub-steps or sub-procedures, in a manner selected from the group consisting of manually, semi-automatically, fully automatically, and combinations thereof, involving use and operation of system units, system sub-units, devices, assemblies, sub-assemblies, mechanisms, structures, components, and elements, and, peripheral equipment, utilities, accessories, and materials. Moreover, according to actual steps or procedures, sub-steps or sub-procedures, system units, system sub-units, devices, assemblies, sub-assemblies, mechanisms, structures, components, and elements, and, peripheral equipment, utilities, accessories, and materials, used for implementing a particular form, the steps or procedures, and sub-steps or sub-procedures are performed by using hardware, software, and/or an integrated combination thereof, and the system units, sub-units, devices, assemblies, sub-assemblies, mechanisms, structures, components, and elements, and peripheral equipment, utilities, accessories, and materials, operate by using hardware, software, and/or an integrated combination thereof.

For example, software used, via an operating system, for implementing certain forms disclosed herein can include operatively interfaced, integrated, connected, and/or functioning written and/or printed data, in the form of software programs, software routines, software subroutines, software symbolic languages, software code, software instructions or protocols, software algorithms, or a combination thereof. For example, hardware used for implementing certain forms disclosed herein can include operatively interfaced, integrated, connected, and/or functioning electrical, electronic and/or electromechanical system units, sub-units, devices, assemblies, sub-assemblies, mechanisms, structures, components, and elements, and, peripheral equipment, utilities, accessories, and materials, which may include one or more computer chips, integrated circuits, electronic circuits, electronic sub-circuits, hard-wired electrical circuits, or a combination thereof, involving digital and/or analog operations. Certain forms disclosed herein can be implemented by using an integrated combination of the just described exemplary software and hardware.

In certain forms disclosed herein, steps or procedures, and sub-steps or sub-procedures can be performed by a data processor, such as a computing platform, for executing a plurality of instructions. Optionally, the data processor includes volatile memory for storing instructions and/or data, and/or includes non-volatile storage, for example, a magnetic hard-disk and/or removable media, for storing instructions and/or data. Optionally, certain forms disclosed herein include a network connection. Optionally, certain forms disclosed herein include a display device and a user input device, such as a touch screen device, keyboard and/or mouse.

BRIEF DESCRIPTION OF THE DRAWINGS

The forms disclosed herein are illustrated by way of example, and not by way of limitation, for the case of processing tobacco for use in manufactured tobacco products in the figures of the accompanying drawings and in which like reference numerals refer to similar elements and in which.

DETAILED DESCRIPTION

Figure 1:
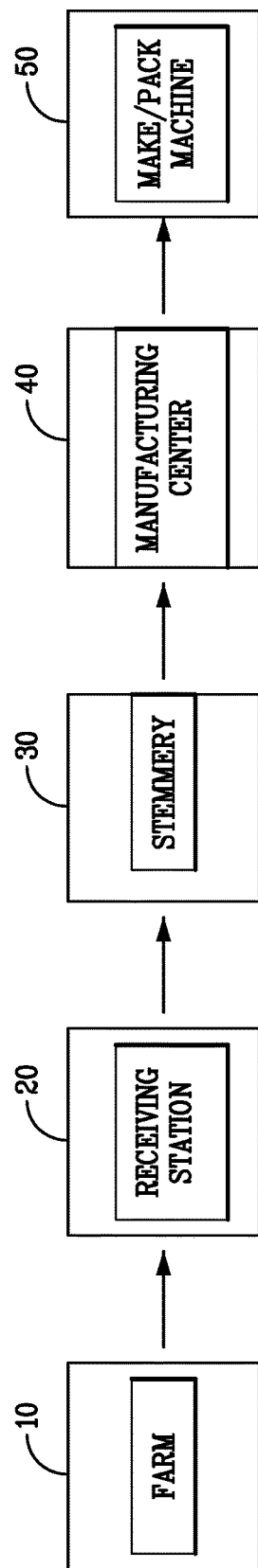
FIG. 1 is a block diagram showing the various stages in the process of cigarette manufacturing.

Various aspects will now be described with reference to specific forms selected for purposes of illustration. It will be appreciated by those skilled in the art that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-5, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways, as can be appreciated by those skilled in the art.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Moreover, all technical and scientific words, terms, and/or phrases, introduced, defined, described, and/or exemplified, in the above sections, are equally or similarly applicable in the illustrative description, examples and appended claims.

Steps or procedures, sub-steps or sub-procedures, and, equipment and materials, system units, system sub-units, devices, assemblies, sub-assemblies, mechanisms, structures, components, elements, and configurations, and, peripheral equipment, utilities, accessories, and materials, as well as operation and implementation, of exemplary forms, alternative forms, specific configurations, and, additional and optional aspects, characteristics, or features, thereof, of the methods, and of the systems, disclosed herein, are better understood with reference to the following illustrative description and accompanying drawings. Throughout the following illustrative description and accompanying drawings, same reference notation and terminology (i.e., numbers, letters, and/or symbols), refer to same system units, system sub-units, devices, assemblies, sub-assemblies, mechanisms, structures, components, elements, and configurations, and, peripheral equipment, utilities, accessories, and materials, components, elements, and/or parameters.

As a means of illustration, the system will be described for application during tobacco processing, but substantially the same system could be applied during the processing of other agricultural products. The detection and separation system disclosed herein can be used in many processes and for consumer products which are susceptible to the presence of unwanted materials during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, lumber or any other manufactured or packaged product wherein an absence of oil is desired.

Referring now to FIG. 1, a block diagram showing the various stages in the process of cigarette manufacturing is presented. As shown, tobacco is first harvested at farm 10, which, in the case of tobacco for use in cigarette manufacturing or the production of moist smokeless tobacco (MST), will be harvested at least in part by machinery. Tobacco in the form of leaf is baled and received at a receiving station 20 from farm 10. Again, the opportunity exists for the tobacco bale to come in contact with lubricated machinery at receiving station 20. The baled tobacco may be transferred to a stemmery 30 wherein large stems are removed by machines to produce destemmed tobacco. The destemmed tobacco is packed into bales which are then stored for a suitable time period of up to several years. Destemmed tobacco is then transferred to manufacturing center 40, wherein various types of tobacco strip may be machine blended according to a predetermined recipe. The blended tobacco may be treated by adding various flavorants to provide a cased tobacco, which is cut at 20-40 cuts per inch to provide tobacco "cut filler." Various other types of tobacco can be added to the cut filler including puffed tobacco, reconstituted tobacco, tobacco reclaimed from rejected cigarettes, and the like, to provide a final product blend. The blend may be then fed to make/pack machine 50, which includes a continuous cigarette rod making apparatus. The continuous rod is then cut, optionally tipped, and packed, typically through the use of high-speed machinery.

As may be appreciated from the above description, in tobacco processing, tobacco comes into contact with machinery at many different points in the overall process, such as machinery used during the growing and harvesting operations on the farm, handling equipment at the receiving station or auction house, machinery in the stemmery, on conveyors, conditioners, cutters and silos in the primary manufacturing centers, and ultimately on makers, tippers and packers in the make/pack manufacturing centers.

The forms disclosed herein are generally focused on the domains encompassing the manufacturing or processing of tobacco, blend components or samples, and are specifically focused on the domains encompassing the automatic monitoring of tobacco processing, performed via hyperspectral imaging and analysis. However, it should be understood that the forms disclosed herein could be applied to other domains encompassing the manufacturing or processing of tea, fruits, during the production of fruit juices, grapes for the production of wines, as well as a vast array of other agricultural products.

In hyperspectral imaging, a field of view of a sample is scanned and imaged while the sample is exposed to electromagnetic radiation. During the hyperspectral scanning and imaging there is generated and collected relatively large numbers of multiple hyperspectral images, one-at-a-time, but, in an extremely fast sequential manner of the objects emitting electromagnetic radiation at a plurality of wavelengths and frequencies, where the wavelengths and frequencies are associated with different selected portions or bands of an entire hyperspectrum emitted by the objects. A hyperspectral imaging and analysis system can be operated in an extremely rapid manner for providing exceptionally highly resolved spectral and spatial data and information of an imaged sample of matter, with high accuracy and high precision, which are fundamentally unattainable by using standard spectral imaging and analysis.

In general, when electromagnetic radiation in the form of light, such as that used during hyperspectral imaging, is incident upon an object, the electromagnetic radiation is affected by one or more of the physical, chemical, and/or biological species or components making up the object, by any combination of electromagnetic radiation absorption, diffusion, reflection, diffraction, scattering, and/or transmission, mechanisms. Moreover, an object whose composition includes organic chemical species or components, ordinarily exhibits some degree of fluorescent and/or phosphorescent properties, when illuminated by some type of electromagnetic radiation or light, such as ultra-violet (UV), visible (VIS), or infrared (IR), types of light. The affected electromagnetic radiation, in the form of diffused, reflected, diffracted, scattered, and/or transmitted, electromagnetic radiation emitted by the object is directly and uniquely related to the physical, chemical, and/or biological properties of the object, in general, and of the chemical species or components making up the object, in particular, and therefore represents a unique spectral fingerprint or signature pattern type of identification and characterization of the object.

A typical hyperspectral imaging system consists of an automated measurement system and corresponding analysis software. The automated measurement system includes optics, mechanics, electronics, and peripheral hardware and software, for irradiating, typically using an illuminating source, a scene or sample, followed by measuring and collecting light emitted, for example, by fluorescence, from objects in the scene or sample, and for applying calibration techniques best suited for extracting desired results from the measurements. Analysis software includes software and mathematical algorithms for analyzing, displaying, and presenting, useful results about the objects in the scene or sample in a meaningful way.

The hyperspectral image of a scene or a sample may be obtained by using one or more commercially available hyperspectral imaging cameras, such as those obtainable from Surface Optics Corporation of San Diego, Calif., or others, or custom built according to the user needs.

Hyperspectral imaging can be thought of as a combination of spectroscopy and imaging. In spectroscopy spectrum is collected at a single point. Spectra contain information about the chemical composition and material properties of a sample, and consist of a continuum of values that correspond to measurements at different wavelengths of light. In contrast, traditional cameras collect data of thousands of points. Each point or pixel contains one value (black and white image) or three values for a color image, corresponding to colors, red, green, and blue. Hyperspectral cameras combine the spectral resolution of spectroscopy and the spatial resolution of cameras. They create images with thousands of pixels that contain an array of values corresponding to light measurements at different wavelengths. Or, in other words, the data at each pixel is a spectrum. Together the pixels and the corresponding spectra create a multi-dimensional image cube. The amount of information contained in an image cube is immense, and provides a very detailed description of the underlying sample.

Each hyperspectral image is a three dimensional data set of voxels (volume of pixels) in which two dimensions are spatial coordinates or position, (x, y), in an object and the third dimension is the wavelength, ($\lambda$), of the emitted light of the object, such that coordinates of each voxel in a spectral image may be represented as (x, y, $\lambda$). Any particular wavelength, ($\lambda$), of imaged light of the object is associated with a set of spectral images each featuring spectral fingerprints of the object in two dimensions, for example, along the x and y directions, whereby voxels having that value of wavelength constitute the pixels of a monochromatic image of the object at that wavelength. Each spectral image, featuring a range of wavelengths of imaged light of the object is analyzed to produce a two dimensional map of one or more physicochemical properties, for example, geometrical shape, form, or configuration, and dimensions, and/or chemical composition, of the object and/or of components of the object, in a scene or sample.

Spectral profiles treat image cubes as a collection of spectra and provide a detailed and comprehensive description of the image cube as a whole. They use a set of characteristic spectra and their relative occurrences within an image cube to summarize the material composition of the sample. The number of characteristic spectra extracted will depend upon the variability in the material, and normally range from a few to a few dozen. Spectral profiles are created by matching each spectra in an image cube to a characteristic spectra. The number of spectra matched to each characteristic spectra are counted and normalized to create the spectral profile of an image cube. Thus, spectral profiles can be thought of as a fingerprint derived from the hyperspectral image cube of the tobacco sample.

In hyperspectral imaging, multiple images of each object are generated from object-emitted electromagnetic radiation having wavelengths and frequencies associated with different selected parts or bands of an entire spectrum emitted by the object. For example, hyperspectral images of an object are generated from object emitted electromagnetic radiation having wavelengths and frequencies associated with one or more of the following bands of an entire spectrum emitted by the object: the visible band, spanning the wavelength range of about 400-700 nanometers, the infra-red band, spanning the wavelength range of about 700-3000 nanometers, and the deep infra-red band, spanning the wavelength range of about 3-12 microns. If proper wavelengths and wavelength ranges are used during hyperspectral imaging, data and information of the hyperspectral images could be optimally used for detecting and analyzing by identifying, discriminating, classifying, and quantifying, the imaged objects and/or materials, for example, by analyzing different signature spectra present in pixels of the hyperspectral images.

A high speed hyperspectral imaging system is often required for different types of repeatable and non-repeatable chemical and physical processes taking place during the sub-100 millisecond time scale, which cannot, therefore, be studied using regular hyperspectral imaging techniques. Combustion reactions, impulse spectro-electrochemical experiments, and inelastic polymer deformations, are examples of such processes. Remote sensing of objects in distant scenes from rapidly moving platforms, for example, satellites and airplanes, is another example of a quickly changing observable that is often impossible to repeat, and therefore requires high speed hyperspectral imaging.

Disclosed herein is a method for detecting foreign matter (including oil or lubricant in product) within an agricultural product stream, such as tobacco, via hyperspectral imaging and analysis. In certain forms thereof, provided are methodologies, protocols, procedures and equipment that are highly accurate and highly precise, in that they are reproducible and robust, when evaluating agricultural products, such as tobacco. The testing methodologies disclosed herein exhibit high sensitivity, high resolution, and high speed during automatic on-line operation.

Certain forms disclosed herein are specifically focused on the domain encompassing measuring, analyzing, and determining, micro scale properties, characteristics, features, and parameters of agricultural products, such as tobacco, generally with respect to individual tobacco samples, and specifically with respect to single or individual tobacco leaves contained within the tobacco samples, and more specifically with respect to a wide variety of numerous possible physical, chemical, and/or biological properties, characteristics, features, and parameters of single or individual tobacco leaves contained within a given tobacco bale, lot or sample. In one form, provided is a method for removing foreign matter from an agricultural product stream of a manufacturing process employing hyperspectral imaging and analysis.

Certain forms disclosed herein use what will be referred to as "hyperspectrally detectable and classifiable codes." As used herein, a "hyperspectrally detectable and classifiable code" is a micro scale property, characteristic, feature, or parameter of a particular bulk agricultural product, such as a tobacco sample, which is hyperspectrally detectable by hyperspectral imaging and analysis in a manner that the resulting hyperspectral data and information, for example, hyperspectral "fingerprint" or "signature" patterns are usable for classifying at least part of a single or individual tobacco leaf contained within that particular tobacco sample. In turn, the classified part of the single or individual tobacco leaf contained within that particular tobacco sample is usable as part of a procedure for monitoring tobacco processing and may also be used to remove foreign matter from an agricultural product stream.

Accordingly, a "hyperspectrally detectable and classifiable code" is defined, generally with respect to a particular individual agricultural product, such as a tobacco sample, and specifically with respect to a single or individual tobacco leaf contained within the particular tobacco sample, and more specifically with respect to a physical, chemical, and/or biological property, characteristic, feature, or parameter, of that single or individual tobacco leaf contained within that particular tobacco sample. The hyperspectrally detectable and classifiable codes are usable as part of a procedure for monitoring the processing or manufacturing of an agricultural product, such as tobacco.

Primary examples of micro scale testing for generating hyperspectrally detectable and classifiable codes, include: physical (geometrical/morphological) shape or form and size dimensions of single or individual tobacco leaves; coloring of single or individual tobacco leaves; moisture (water) content of, or within, single or individual tobacco leaves; type, distribution, and compositional make-up, of (organic and inorganic) chemical species or components, of single or individual tobacco leaves; types, distribution, and compositional make-up, of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects, such as exposure to aqueous liquids or to non-aqueous (organic based) liquids; and activity and/or reactivity of single or individual tobacco leaves in response to biological stimuli or effects, such as exposure to biological organisms; physical (geometrical/morphological) shape or form and size dimensions of single or individual tobacco leaves; coloring of single or individual tobacco leaves; moisture content of, or within, single or individual tobacco leaves; types, distribution, and compositional make-up, of (organic and inorganic) chemical species or components, of single or individual tobacco leaves; types, distribution and compositional make-up of possible unknown or foreign (physical, chemical, and/or biological) matter or species and aspects thereof on, and/or within, single or individual tobacco leaves; activity and/or reactivity of single or individual tobacco leaves in response to physical stimuli or effects, such as exposure to electromagnetic radiation; activity and/or reactivity of single or individual tobacco leaves in response to chemical stimuli or effects (such as exposure to aqueous (water based) liquids or to non-aqueous (organic based) liquids); and activity and/or reactivity of single or individual tobacco leaves in response to biological stimuli or effects, such as exposure to biological organisms.

Accordingly, provided is a method for removing foreign matter (including oil or lubricant in product) from an agricultural product stream of a manufacturing process. The method includes conveying a product stream past an inspection station; scanning a region of the agricultural product stream as it passes the inspection station using at least one light source of a single or different wavelengths; generating hyperspectral images from the scanned region; determining a spectral fingerprint for the agricultural product stream from the hyperspectral images; comparing the spectral fingerprint obtained in step (c) to a spectral fingerprint database containing a plurality of fingerprints using a computer processor to determine whether foreign matter is present and, if present, generating a signal in response thereto; and removing a portion of the conveyed product stream in response to the signal.

The method is based upon obtaining hyperspectral signatures for the agricultural material being processed to minimize or eliminate the need for human evaluation during processing. To accomplish this, first a standard database is created that includes hyperspectral signatures taken at the location of an inspection station. The database so obtained is used as a benchmark against which the process will be monitored.

The method may comprise scanning multiple regions along the sample of agricultural product using at least one light source of a single or different wavelengths; and generating hyperspectral images from the multiple regions. The method may further comprise determining a code.

The agricultural product may comprise tobacco. The tobacco may be in the form of a sample. At least one light source may be positioned to minimize the angle of incidence of each beam of light with the tobacco.

The method may further comprise repeating the steps of scanning at least one region along a sample of agricultural product using at least one light source of different wavelengths, generating hyperspectral images from the at least one region, and forming a spectral fingerprint for the sample of agricultural product from the hyperspectral images, for a plurality of samples of agricultural product during the processing of the agricultural product.

The method may further comprise storing spectral fingerprints data from a plurality of samples of agricultural product taken at various stages of processing within computer storage means to form a process database.

The method may further comprise storing data about the spectral fingerprint within a computer storage means, and repeating the steps of scanning multiple regions along a sample of a desirable agricultural product using at least one light source of a single or different wavelengths, generating hyperspectral images from the multiple regions, forming a spectral fingerprint for the sample from the hyperspectral images, storing data about the spectral fingerprint within a computer storage means, using a plurality of desirable agricultural products. The desirable agricultural product may be an unprocessed, semi-processed or fully processed agricultural product, such as tobacco.

While the invention is described in detail for the case of tobacco, it should be understood that tobacco is used only to illustrate the methods and systems contemplated herein and not so as to limit the application of the methods and systems described herein.

Figure 2:
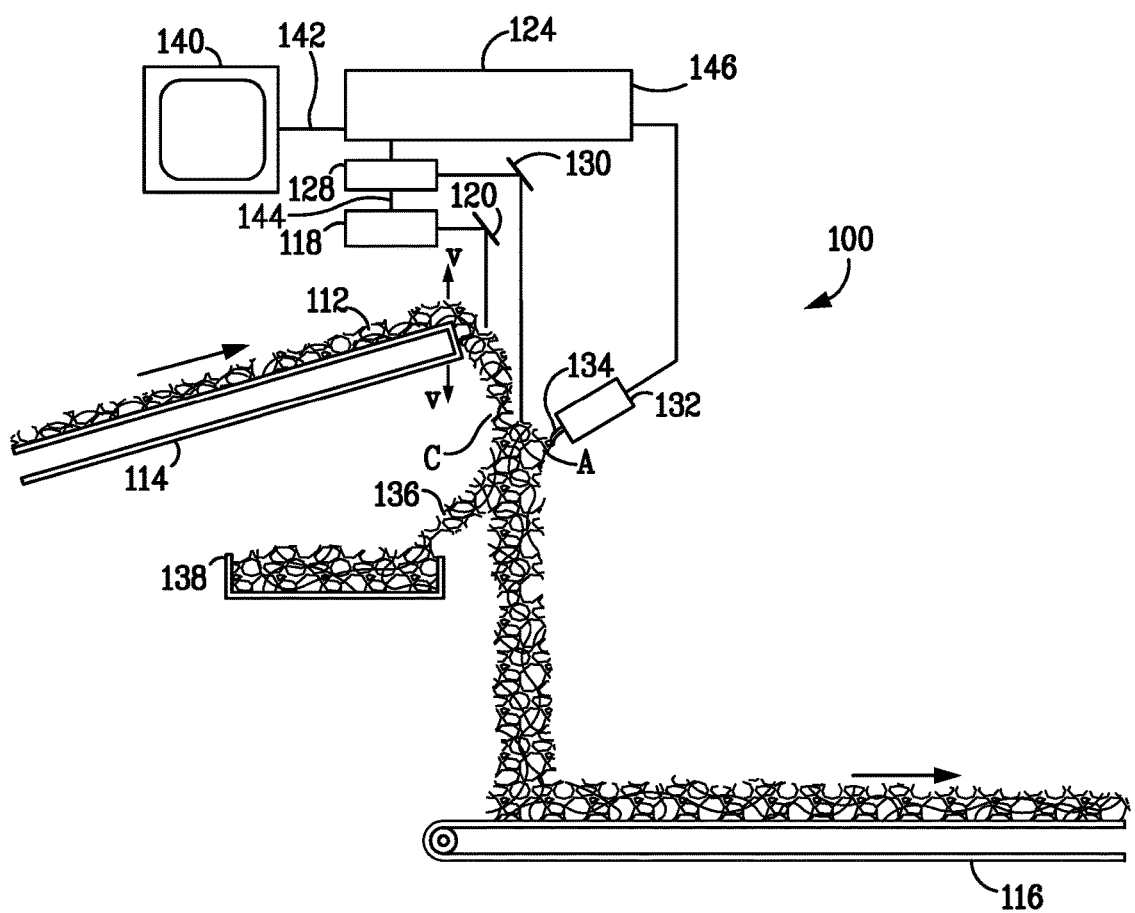
FIG. 2 presents a schematic representation of a detection and separation system, in accordance herewith.

Referring now to FIG. 2, one form of a detection and separation system 100, as disclosed herein, is shown schematically. In operation, an agricultural product stream 112, which may be a tobacco stream, containing foreign material, such as foil, cellophane, warehouse tags, and paper, or oil or lubricant containing material, is delivered from a processing line by conveyor 114. Conveyor 114 is preferably a vibrating inclined conveyor which vibrates as shown by arrows V. In one form, conveyor 114 ends above another conveyor 116, which can be an ordinary conveyor belt, and is spaced vertically above conveyor 116 a sufficient distance to accommodate the remainder of the system described below. As product stream 112 reaches the end of conveyor 114, it drops under the influence of gravity in a cascade C to conveyor 116. In one form, because conveyor 114 is inclined, the product stream does not have as great a horizontal velocity when it falls, so that cascade C does not have any significant front-to-back horizontal spread.

In another form, detection and separation system 100 may include a single conveyor 114 for inspecting finished product, such as cigarettes, smokeless tobacco containers, SNUS pouches, etc., with product rejection, described in more detail below, taking place on the same conveyor.

The detection and separation system 100 includes at least one light source 118 for providing a beam of light. As shown, the at least one light source 118 may be mounted on an arm 144 for positioning at least one light source 118 in proximity to the product stream 112. In one form, arm 144 may be mounted to cabinet 146 and may be either fixed thereto or moveably positionable, as will be described hereinbelow. A second light source (not shown) may also be provided and mounted to cabinet 146 or, optionally, to another arm (not shown), which in turn may be mounted to cabinet 146.

In some forms, the at least one light source 118 for providing a beam of light of different wavelengths comprises a tungsten, halogen or a xenon light source. In another form, the at least one light source 118 for providing a beam of light comprises a mercury light source. In yet another form, the at least one light source 118 or the second light source (not shown) comprises an ultraviolet light source for use in providing a chemical signature of the agricultural product stream 112. This optional ultraviolet light source adds an additional media of classification that provides a better understanding of an agricultural product's characteristics. In still yet another form, the at least one light source 118 comprises a xenon light source, the second light source (not shown) comprises a mercury light source and a third light source (not shown) comprises an ultraviolet light source.

As shown in FIG. 2, the light from the at least one light source 118 may be directed toward the cascade C of the product stream $P_0$ by the mirror 120. The hyperspectral image of a scene or a sample is obtained using hyperspectral imaging camera 128, which, in some forms, may receive light reflected by mirror 130, as shown.

In some forms, the at least one light source 118 and/or the second light source (not shown) may be positioned to minimize the angle of incidence of a beam of light with the agricultural product stream $P_0$.

In order to segregate ambient light from the light provided by system 100, walls (not shown) may be added to form an enclosure to provide a dark-room-like environment for system 100.

Referring still to FIG. 2, a computer 124 may be mounted with cabinet 146. The computer 124 is provided with a processor capable of rapidly handling system data and programmed to compare the detected component wavelengths to a database of previously analyzed agricultural products. Computer 124 may be a personal computer having an Intel® Core™2 Quad or other processor. Computer 124 may also control the operation of the system 100. A device for providing an uninterrupted source of power to computer 124 may be provided and mounted within cabinet 146, such devices readily available from a variety of commercial sources. A regulated power supply (not shown) may be provided to assure that a tightly controlled source of power is supplied to system 10.

In one form, system 100, is provided with a user interface 140 that enables an operator (not shown) to observe and control various operational aspects of the system 100. The user interface 140 may include a CRT or LCD panel for output display. For input, the user interface 140 may include a keyboard, touch-screen or other input means known in the art. The operator can view representations of the articles in the product stream 112 as they are processed in system 100 on the user interface 140. Yet further, the user interface 140 provides a means for the operator to configure the operation of system 100 to make a determination between acceptable product and undesirable product. Data gathered by the user interface 140 and provided to the user interface are transported as user interface data 142.

When system 100 detects foreign material in product stream 112, computer 124 sends a signal to ejector manifold 132, which is positioned in downstream relation to the region illuminated by the at least one light 118. Ejector manifold 132 is in fluid transmission relation to the trajectory of the product stream 112. The ejector manifold 132 includes a plurality of ejector nozzles 134, which are individually directed and controlled to selectively remove undesirable product material 136 from the product stream 112. The ejector nozzles 134 act as conduits for directing fluid pulses to dislodge or otherwise re-direct product material traveling in the trajectory. Individual ejector nozzles 134 contained in the ejector manifold 132 are driven by a plurality of removal signals, which may be provided by processor 124.

Ejector nozzles 134 are connected to a source of high pressure fluid which is preferably air at approximately 80 psi, although other gases, such as steam, or liquids, such as water, can be used. When one of ejector nozzles 134 opens in response to a signal, a blast of air A is directed against that portion of cascade C in which the foreign material was detected to force that portion 136 of the product stream and/or foreign material to fall into receptacle 138 for manual sorting, if necessary. In the case of usable product, it may be returned to the product processing line upstream or downstream of system 100, depending on whether or not rescanning is desired. Alternatively, portion 136 could be deflected to a conveyor that removes it to another area for processing.

As may be appreciated, system 100 allows tobacco or other materials to be processed at greater rates than a system in which the tobacco or other materials are scanned on a belt conveyer. This is because when product is optically scanned on a belt, it has to be in a "monolayer," or single layer of particles, for all of the particles on the belt to be visible to the hyperspectral imaging camera 128. However, as the tobacco or other material falls in cascade C, relative vertical motion between the various particles of tobacco and foreign material is induced by the turbulence of the falling stream, so there is a greater probability that a particular piece of foreign material will be visible to hyperspectral imaging camera 128 at some point in its fall. Relative vertical motion also results if the foreign material is significantly lighter or heavier than tobacco so that it has greater or less air resistance as it falls. Relative vertical motion is enhanced by the vibration of conveyor 114 which brings lighter material to the surface of the tobacco before it falls in cascade C, making the lighter material, which is usually foreign material, easier to detect, as in a monolayer.

The inclination of conveyor 114, in reducing the horizontal spread of cascade C as discussed above, also enhances relative vertical motion because the particles in cascade C have little or no horizontal velocity component. Any horizontal velocity component that a particle has when it falls off conveyor 114 is small because conveyor 114 is inclined, and air resistance quickly reduces the horizontal motion to near zero. The relative vertical motion allows a relatively thicker layer of tobacco or other material to be scanned, so that a greater volume can be scanned per unit of scanning area. Given a constant rate of area scanned per unit time, the increased volume scanned per unit area translates into a higher volume of tobacco or other material scanned per unit time.

Results obtained by system 100 are based on the scanning and counting of individual samples, each comprising dozens of scans, and each sample classified using spectral band features, spectral finger prints (SFP), major spectral representative components, purity and quality of each major compound (component, SFP), relative quantity of each SFP and, optionally, crystallization and morphological features.

In operation, a plurality of samples of agricultural products, such as tobacco samples are scanned, which relate to the location in the manufacturing process where an inspection station employing system 100 will be installed. As indicated, for agricultural products, such as tobacco, a significant number of samples should be scanned in order that the impact of sample variability is reduced. In practice, it has been observed that the impact due to this variability can be reduced when the number of samples N is about 5 to about 25. However, by carefully selecting representative samples, fewer samples could be used to incorporate all the normal variations observed in processing a particular product. Applying this technique to tobacco, tobacco samples may be scanned using xenon and/or mercury and/or tungsten, and/or halogen light sources and an optional ultraviolet light source may be used for chemical signature classification.

In operation, the light source(s) is activated (one, two, three or more spot lights in parallel to the region of interest (ROI)), permitting redundant data to be gathered. A plurality of regions of interest (such as by way of example, but not of limitation, a 20 cm×20 cm area for each ROI) is scanned for each sample to provide one, two, three or more hyperspectral images. Scanning is performed and the reflection spectral signature and optional fluorescence spectral chemical signature received. The images are then saved and a database (including labels identifying the particular sample and/or lot) is thus formed from the combined information obtained for the N samples During scanning, the hyperspectral camera system provides a three dimensional hyperspectral image cube. The image cube, which may be, by way of example, but not of limitation, on the order of about a 696 pixel by 520 pixel array. Such a picture or frame would thus contain 361,920 pixels. As may be appreciated by those skilled in the art, each pixel may contain about 128, 256, 500 or more spectra points at different wavelengths for an agricultural product such as tobacco.

Figure 3:
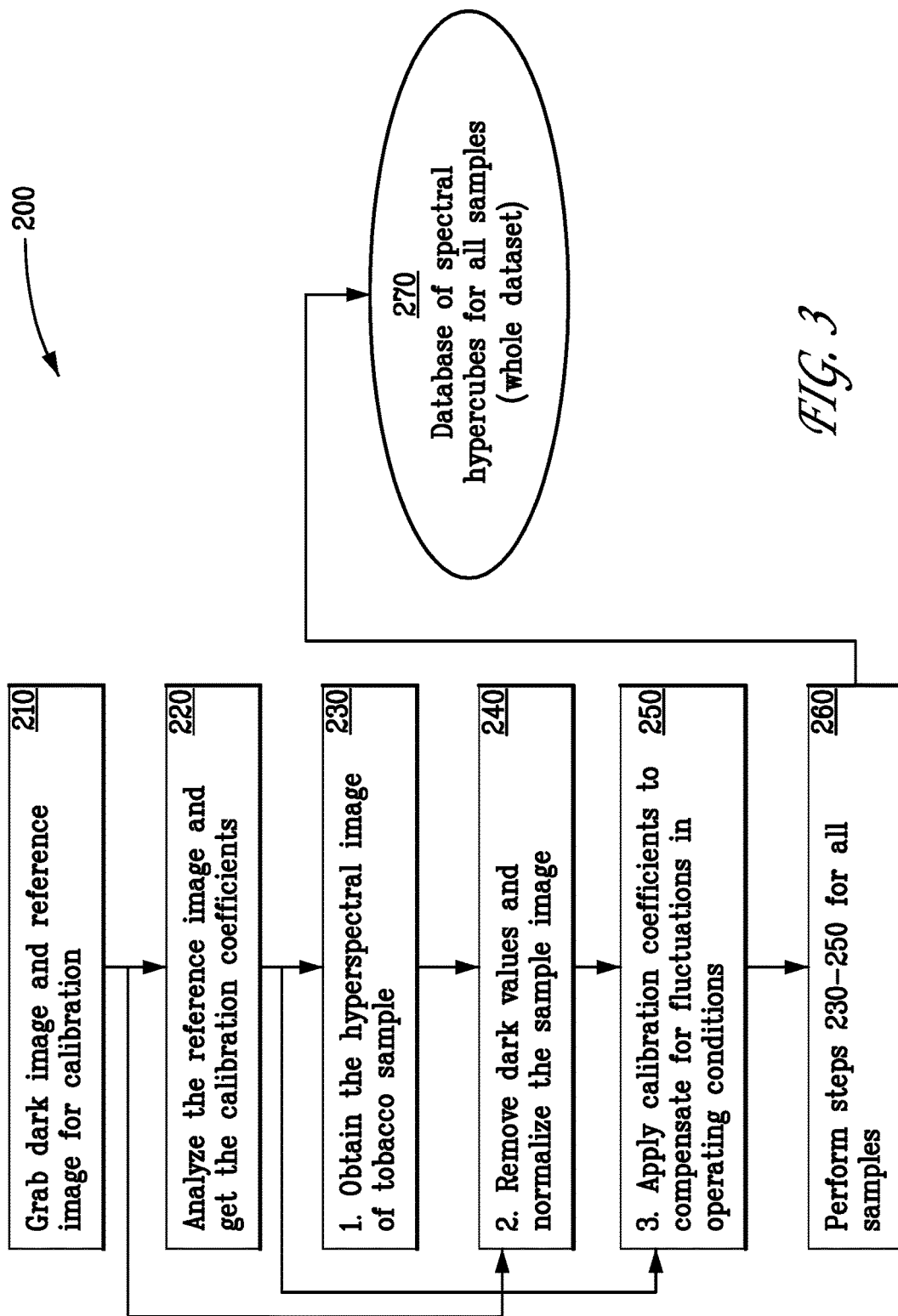
FIG. 3 presents a method for analyzing data to create a spectral library, in accordance herewith.

Referring now to FIG. 3, an algorithm 200 for use in the system and methods described herein will now be disclosed. In step 210, a dark image and reference image are obtained for use in system calibration. In step 220, the reference image is analyzed and calibration coefficients are obtained. In step 230, a hyperspectral image of a tobacco sample is obtained. In step 240, using the information obtained during calibration, dark values are removed and the sample image normalized. In step 250, calibration coefficients are applied to compensate for fluctuations in operating conditions (e.g., light intensity, ambient conditions, etc.). In step 260, steps 230-250 are repeated for all samples and the data so obtained is added in step 270 to the database of spectral hypercubes (whole dataset). It should be understood that the algorithm for creating the database as illustrated in FIG. 3 is referenced to tobacco samples by way of illustration only and not as limiting. The same steps could be used to create the whole spectral database for application in other agricultural products like tea, fruits grapes or other products. The result is 350, a spectral library for all the samples that could be used to assess and monitor processing of the agricultural product, which contains the spectral fingerprints of the dataset found in step 340, and the unique spectra found in step 330.

Figure 4:
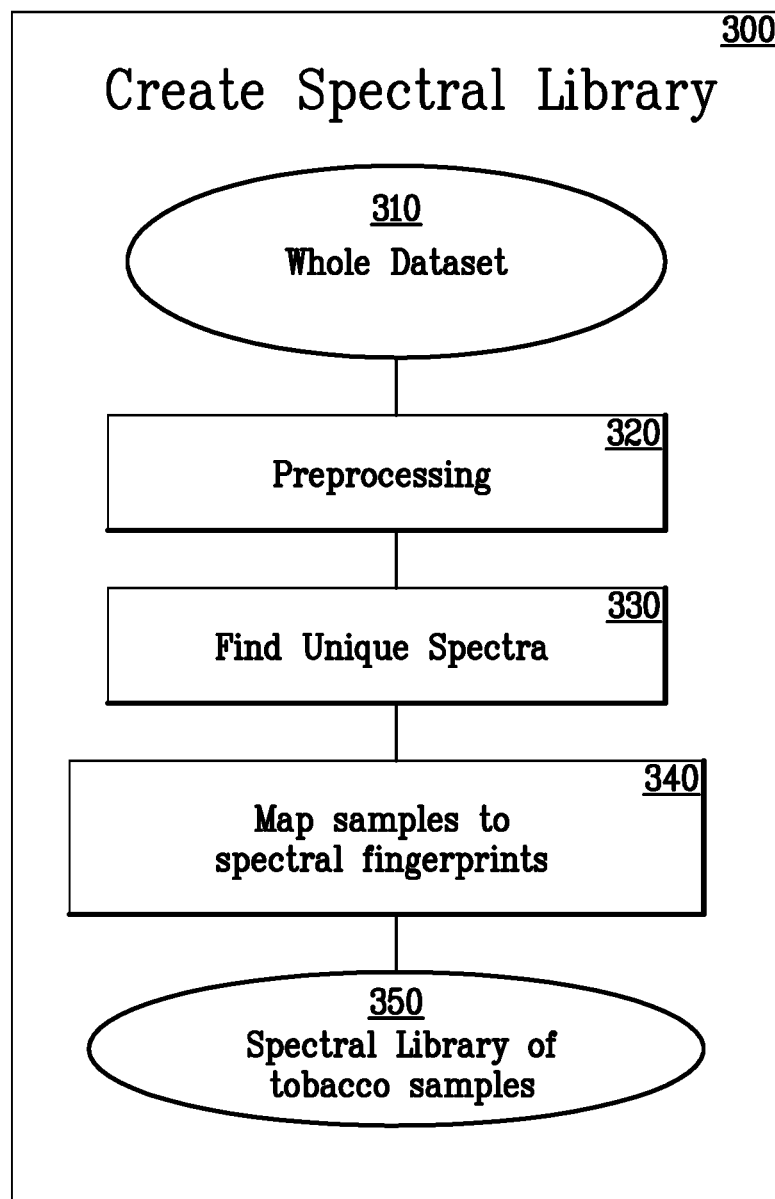
FIG. 4 presents a method for analyzing data to create a spectral library, in accordance herewith.

Referring now to FIG. 4, a method for analyzing data to create a spectral library of samples 300, in accordance herewith is shown. Spectral library 300 is formed by obtaining a dataset in step 310. In step 320, the dataset is preprocessed. Unique spectra, indicative of the dataset, are identified in step 330. In step 340, spectral distributions (spectral fingerprints) are found for each of the samples using the unique spectra found in step 330.

In some forms, following imaging, several data processing routines are performed to reduce noise, increase consistency, enhance spectra for feature extraction, and reduce computation time. The data processing routines are summarized below.

Spectral binning is used to produce more consistent signals, reduce file size, and decrease processing time. Spectral binning is an operation performed on each spectra of the image cube, and consists of summation of adjacent wavelengths to produce a down-sampled spectra. Down-sampled spectra have less resolution, but increased signal to noise ratio. A sampling rate was chosen that creates a signal with maximum compression and minimal loss of fidelity. This is followed by median filtering to reduce the noise and increase the signal to noise ratio.

Spatial Binning is applied to the image cube, and consists of down-sampling via summation of adjacent pixels. Pixels contain spectra, so spatial binning results in summation of adjacent spectra. This increases signal to noise ratio, reduces file size, and decreases processing time. Information loss is minimal because the camera is selected to provide a high resolution. Summation allows for each pixel's spectra to contribute to the down-sampled spectra, and adjacent pixels are usually from the same part of the leaf, which tend to have similar spectra. Similar effects may be achieved by using a Gaussian filter to increase spatial coherency and to reduce "salt and pepper" pixel classification. A Gaussian filter may be useful when spatial reduction is not desirable.

In some forms, image correction may be performed by first collecting dark images twice daily. These are then used during processing to estimate and remove sensor noise. The dark image processing procedure consists of two steps. Dark images' spectra, $\vec{d}_j \in D_i$ are first binned to be consistent with other images cubes. Then the spectral mean, $\vec{d}^{mean;i}$ is calculated (Eq. 1) and used to estimate sensor noise.

$$\vec{s}_i^{mean} = \left\| \sum_{\forall \vec{s}_j \in S_i} \vec{s}_j \right\| \quad (1)$$

During data processing $\vec{d}^{mean;i}$ is removed from each spectra of each sample by subtraction. This is a standard method of removing sensor noise.

Reference image cubes, $R_i$ are collected twice-daily and contain spectra that can be used to measure and correct lighting inconsistencies. Applying a correction based on the reference image will also eliminate any sensor drift or variation over time. This step is very important as any changes in either the lighting conditions or the sensor response drift will adversely affect the system performance. Also, pixels of shadow have low signal to noise ratio and should be eliminated.

Most signals tend to have a maximum peak created by the spectral signature of the light whose value is proportional to the amount of light hitting the sensor, and the sensor's response. For this reason shadow detection is applied using maximum peak threshold ing.

$$pixel = \begin{cases} \text{not shadow:} & \max(\vec{s}_i) \geq \text{thresh} \\ \text{shadow:} & \max(\vec{s}_i) < \text{thresh} \end{cases}$$

where $\max(\vec{s}_i)$ returns the maximum component of the spectra, $\vec{s}_i$.

Spectra with a max peak less than a user-defined threshold are tagged as shadow spectra, and ignored during spatial binning, spectral binning, local spectra extraction, and spectra matching.

Image cubes of tobacco samples contain thousands of spectra, many of which are nearly identical and correspond to similar material properties and sensorial effects. The information contained in the image cube can be summarized as a spectral profile using a set of characteristic spectra and their occurrence rate within a sample. Construction of a spectral profile consists of two primary steps.
1. Spectra Extraction—finding characteristic spectra.
2. Spectra Matching—matching an image cube's spectra to characteristic spectra.

The first step of building a spectral profile is to create a set of characteristic spectra often called end-members. End-members are often manually selected by choosing pixels that are known to correspond to a specific class or contain a unique material. For many agricultural products, including tobacco, distinct characteristics can be very difficult to detect manually and class specific spectra are non-existent. In such cases an automated spectra extraction technique is preferable.

Spectra extraction differs from other automated end-member extraction techniques in that it divides the spectral feature space using an evenly spaced grid. Spectra extraction finds all spectra in a data set that are more dissimilar than a user-defined threshold, $\alpha^*$. The assumption is that if two spectra are more similar than $\alpha^*$ they represent identical materials and can be considered duplicates. By finding all dissimilar spectra in a data set, all unique materials can be found. Other automated spectra extraction algorithms are often associated with un-mixing models, which assume individual pixels contain a combination of unique spectral signatures from multiple materials. Sequential Maximum Angle Convex Cone (SMACC) and Support Vector Machine-Based End-member extraction are two examples. The technique disclosed herein was chosen for simplicity. Un-mixing models may not be appropriate for smaller scale agricultural imaging, where individual pixel size is in millimeters as opposed to aerial imaging, where individual pixel size is usually in meters. The spectra extraction procedure disclosed herein first analyzes image cubes independently in a step called local spectra extraction. The results are then combined during global spectra extraction. Extraction in this order decreases processing time and allows for outliers of individual image cubes to be eliminated.

Once the characteristic spectra of the data set have been extracted, spectra matching step is applied on each image cube. Each $\vec{s}_j \in S_i$ is matched with the most similar $\vec{c}_k \in C_{all}$. As an image cube is analyzed, a tally of the number of matches for each $\vec{c}_k \in C_{all}$ is kept as a spectral profile, $\vec{p}_i$. Each component of corresponds to the number of matches for a single $\vec{c}_k \in C_{all}$. Once all $\vec{s}_j \in S_i$ have been matched $\vec{p}_i$ is normalized and represents the percent occurrence rate of each $\vec{c}_k \in C_{all}$ in Si.

The inclusion of unidentified pixels can be advantageous for certain scenarios such as when tobacco samples contain non-tobacco material, if shadow detection is unreliable, or if only a selected few spectra should be included in the spectral profiles. Rather than forcing a match with the most similar $\vec{c}_k \in C_{all}$, Spectra that are more dissimilar than $\alpha^{}$ to all $\vec{c}_k \in C_{all}$ are counted as unidentified. Unidentified pixels do not contribute to the spectral profile. $\alpha^{}$ is a user-defined parameter, and larger values of $\alpha^{**}$ will allow more dissimilar spectra to match to $\vec{c}_k \in C_{all}$, while small values will allow matches with only similar spectra. Setting a high $\alpha^*$ will force a match with the closest $\vec{c}_k \in C_{all}$.

Since previous hyperspectral image classification problems have focused on pixel by pixel classification, spectra matching is often the goal of hyperspectral image analysis. These applications often make use of machine learning algorithms such as support vector machines and decision trees to classify spectra. Matching in this manner requires a training set of characteristic spectra which is not practical. Fully automated techniques are preferable, and also may use spectral feature fitting (SFF). SFF is designed to distinguish between spectra using specific features of a spectra. While SFF can achieve successful results, spectral angle measure (SAM) is a more appropriate measure, since it is intended to find the similarity between two spectra using all the bands as confirmed by the results.

The goal of feature selection is to choose a subset of features capable of summarizing the data with little or no information loss. It is applied before classification to avoid dimensionality, which often reduces classification performance. Spectral profiles can contain redundant features, particularly when the spectra extraction threshold, $\alpha^*$ is low. Experimental work suggests that selection of an appropriate $\alpha^*$ combined with the ability of support vector machines (SVM) to handle redundant and/or uninformative features eliminates the need for a feature selection step. However in some cases we found that choosing the optimal subset of features using the Jeffreys-Matusita Distance as an information measure was effective.

In some forms, classification may be conducted using well-known procedures, by way of example and not of limitation, discriminant analysis, SVM, neural networks, etc., as those skilled in the art will recognize.

As may be appreciated, the amount of raw data is very large, due to the large number of pixels existing within a particular image cube. A separate spectral is obtained for each pixel. Advantageously, the method disclosed herein identifies a set of characteristic spectra for the whole dataset. The composition of the spectra provides a signature for the sample, with similar samples having similar signatures or fingerprints. Unique spectral fingerprints are then identified for each tobacco sample.

The spectral library or database of the samples developed in FIG. 4 may be used to determine whether foreign matter is present in an agricultural product stream. This information may also be used in a closed system capable of separating foreign matter from the agricultural product stream, as disclosed herein.

Advantageously, the method and system disclosed herein provides a chemical imaging platform that enables speed and exceptionally high sensitivity, thus accurate and non-destructive nature, wherein measurement time is greatly reduced. This enables the tracking of the monitored material with high repeatability.

The method and system disclosed herein provides a highly sensitive hyper spectral imaging analyzer with co-sharing database capabilities. The digitized highly sensitive imaging system disclosed herein enables the imaging of materials components, more detailed observation and provides more specific, sensitive, accurate and repeatable measurements. This may be achieved using advanced image recognition technologies, as well as adaptive and collaborative data bases and statistical and optimization algorithms.

The method and system disclosed herein is capable of characterizing the composition of inorganic, organic, and chemical particulate matter suspended in agricultural products such as tobacco. The instrument scans leaf or other samples, analyses the scanned samples' wavelength signature, performing trends analysis and compares the gathered data to data bases that may, in one form, be continuously updated. The system then generates reports for system users. A remote network may be provided to support the gathering of data for integrated database construction as well as to support remote professional personnel in real time.

Advantageously, the proposed method requires no sample preparation. In operation, linear calibration plots in the ppm range are obtained for the presence of mono-components and for simple compound mixtures in this matrix. Non-contact, non-destructive, near real time on-line, automated physicochemical imaging, classification and analysis of a sample of tobacco leaves or other agricultural products is provided without the need for consumable materials for sample processing. The system operates using algorithms and software packages, together with unique ultra-high resolution optical components and a two-dimensional sample positioning of regions of interest for generating, for example, five dimensional (5D) spectral images of the tobacco sample under analysis.

All or a portion of the devices and subsystems of the exemplary forms can be conveniently implemented using one or more general purpose computer systems, microprocessors, digital signal processors, microcontrollers, and the like, programmed according to the teachings of the exemplary forms disclosed herein, as will be appreciated by those skilled in the computer and software arts.

In view thereof, in one form there is provided a computer program product for monitoring a manufacturing process of an agricultural product, the computer program structured and arranged to determine whether foreign matter is present in an agricultural product stream, including one or more computer readable instructions embedded on a tangible computer readable medium and configured to cause one or more computer processors to perform the steps described above and transmitting information relating to the steps described above over a communications link.

Appropriate software can be readily prepared by programmers of ordinary skill based on the teachings of the exemplary forms, as will be appreciated by those skilled in the software art. Further, the devices and subsystems of the exemplary forms can be implemented on the World Wide Web. In addition, the devices and subsystems of the exemplary forms can be implemented by the preparation of application-specific integrated circuits or by interconnecting an appropriate network of conventional component circuits, as will be appreciated by those skilled in the electrical art(s). Thus, the exemplary forms are not limited to any specific combination of hardware circuitry and/or software.

Stored on any one or on a combination of computer readable media, the exemplary forms disclosed herein can include software for controlling the devices and subsystems of the exemplary forms, for driving the devices and subsystems of the exemplary forms, for enabling the devices and subsystems of the exemplary forms to interact with a human user, and the like. Such software can include, but is not limited to, device drivers, firmware, operating systems, development tools, applications software, and the like. Such computer readable media further can include the computer program product of a form disclosed herein for performing all or a portion (if processing is distributed) of the processing performed in implementing the methods disclosed herein. Computer code devices of the exemplary forms disclosed herein can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the exemplary forms disclosed herein can be distributed for better performance, reliability, cost, and the like.

As stated above, the devices and subsystems of the exemplary forms can include computer readable medium or memories for holding instructions programmed according to the forms disclosed herein and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

The forms disclosed herein, as illustratively described and exemplified hereinabove, have several beneficial and advantageous aspects, characteristics, and features. The forms disclosed herein successfully address and overcome shortcomings and limitations, and widen the scope, of currently known teachings with respect to the processing of agricultural products such as tobacco.

The forms disclosed herein, provide for processing methodologies (protocols, procedures, equipment) for, by way of example, but not of limitation, tobacco samples, which are highly accurate and highly precise (reproducible, robust). The forms disclosed herein, provide high sensitivity, high resolution, and high speed (fast, at short time scales), during automatic operation, in an optimum and highly efficient (cost effective) commercially applicable manner.

As may be appreciated, the performance of the methods and systems disclosed herein is dependent of the number of regions and samples scanned, image sizes, light sources, filters, light source energy stability, etc.

EXAMPLES

Example 1

The operation of the system and a method of forming a database will now be described.

The system was initiated and the light sources brought up to operating temperature. A dark image and reference image was obtained for system calibration. The reference image was analyzed and calibration coefficients obtained. A hyperspectral image of a tobacco sample was obtained.

Using the information obtained during the aforementioned calibration, dark values were removed and the sample image normalized. Calibration coefficients were applied to compensate for fluctuations in operating conditions (e.g., light intensity, ambient conditions, etc.). Hyperspectral images for additional tobacco samples, and NTRM samples were obtained for additional samples of interest and all data so obtained is added to the database of spectral hypercubes (whole dataset).

A spectral library was formed from the database of spectral hypercubes by first preprocessing the data. Unique spectra, indicative of the dataset were identified and samples mapped to the spectral fingerprints so obtained. The unique spectra were then added to a spectral database.

Figure 5:
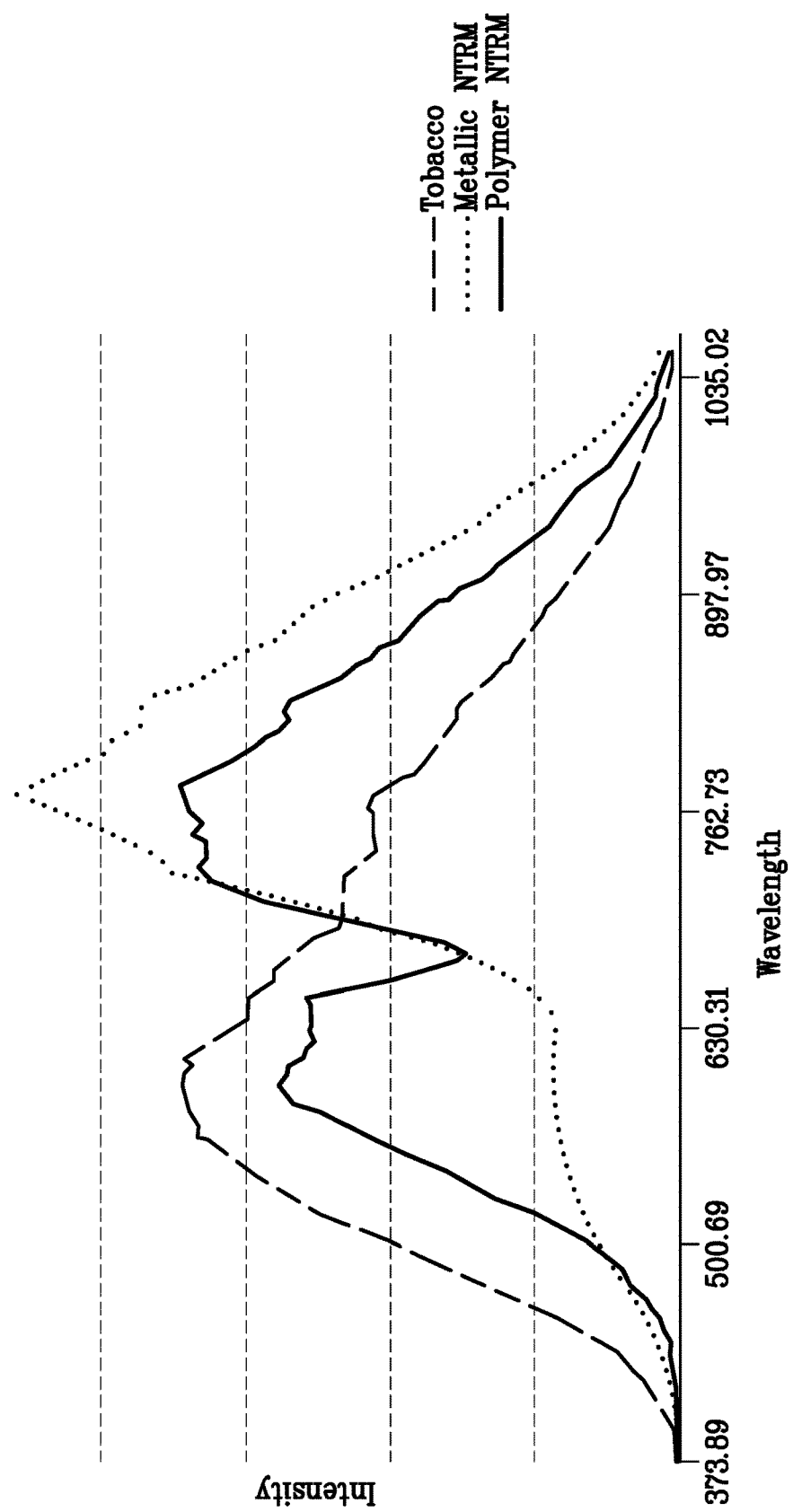
FIG. 5 presents a graph of intensity as a function wavelength for tobacco and non-tobacco related materials, the graph produced in accordance herewith.

From the data so obtained, a graph of intensity as a function of wavelength for tobacco and non-tobacco related material is presented in FIG. 5. As may be seen, sharp distinctions were observed for tobacco and polymeric and metallic NTRM.

Example 2

A method for using the database created, in accordance herewith, will now be described by way of this prophetic example.

When a new batch of agricultural product is to be processed, first, a spectral distribution is obtained for this product based on the teachings of this invention. As described herein, a selection algorithm is used, the results of which provide the parameters necessary to determine whether foreign matter is present in an agricultural product stream. Such material may be isolated and removed from the product stream in response to the determination.

Upon implementation in accordance with the foregoing teachings, the system will lessen or obviate the need for off-line sampling in the quality control of commercially manufactured agricultural products.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

Illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1 A method for removing foreign matter from an agricultural product stream of a manufacturing process, the method comprising the steps of: (a) conveying a product stream past an inspection station; (b) scanning a region of the agricultural product stream as it passes the inspection station using at least one light source of a single or different wavelengths; (c) generating hyperspectral images from the scanned region; (d) determining a spectral fingerprint for the agricultural product stream from the hyperspectral images; (e) comparing the spectral fingerprint obtained in step (c) to a spectral fingerprint database containing a plurality of fingerprints using a computer processor to determine whether foreign matter is present and, if present, generating a signal in response thereto; and (f) removing a portion of the conveyed product stream in response to the signal.

A2. The method of paragraph A1, further comprising the step of causing the portion of the conveyed product stream to fall under the influence of gravity in a cascade.

A3. The method of paragraph A2, wherein the cascade is a turbulent cascade.

A4. The method of paragraph A2, wherein said step of removing a portion of the conveyed agricultural product stream in response to the signal further includes directing fluid under pressure at the portion of the agricultural product stream.

A5. The method of paragraph A4, wherein the fluid is a gas.

A6. The method of paragraph A5, wherein the gas is pressurized air.

A7. The method of paragraph A1, wherein the agricultural product is tobacco.

A8. The method of paragraph A1, wherein the agricultural product is tea.

A9. The method of paragraph A1, wherein the at least one light source is positioned to minimize the angle of incidence of each beam of light with the agricultural product stream.

A10. The method of paragraph A1, wherein the at least one light source for providing a beam of light comprises a light source selected from the group consisting of a tungsten light source, a halogen light source, a xenon light source, a mercury light source, an ultraviolet light source, and combinations thereof.

B1. A system for detecting foreign matter within a agricultural product stream, comprising: (a) a first conveying means for delivering a product stream; (b) an inspection station comprising (i) at least one light source of a single or different wavelengths for providing a beam of light to scan a region of the agricultural product stream as it passes the inspection station, and (ii) a hyperspectral camera system for providing a three dimensional hyperspectral image cube; (c) a computer processor structured and arranged to determine a spectral fingerprint for the agricultural product stream from the hyperspectral image cube and to compare the spectral fingerprint obtained to a spectral fingerprint database containing a plurality of fingerprints to determine whether foreign matter is present and, if present, generating a signal in response thereto.

B2. The system of paragraph B1, further comprising at least one deflecting system responsive to the signals obtained from said computer processor, said at least one deflecting system directing fluid under pressure at a portion of the product stream when said computer processor determines that foreign matter is present in the product stream.

B3. The system of paragraph B2, wherein the fluid so directed is effective to remove the foreign matter.

B4. The system of paragraph B3, further comprising a second conveying means located below and spaced vertically from said first conveying means for further conveying the product stream from said first conveying means, wherein said product stream is transferred from said first conveying means to said second conveying means by falling therebetween under the influence of gravity in a cascade.

B5. The system of paragraph B4, wherein the cascade is a turbulent cascade.

B6. The system of paragraph B1, wherein said first conveying means is an inclined vibrating conveyor.

B7. The system of paragraph B1, wherein the fluid is a gas.

B8. The system of paragraph B7, wherein the gas is air.

B9. The system of paragraph B1, wherein the agricultural product is tobacco.

B10. The system of paragraph B1, wherein the agricultural product is tea.

B11. The system of paragraph B1, wherein the at least one light source is positioned to minimize the angle of incidence of each beam of light with the agricultural product stream.

B12. The system of paragraph B1, wherein the at least one light source for providing a beam of light comprises a light source selected from the group consisting of a tungsten light source, a halogen light source, a xenon light source, a mercury light source, an ultraviolet light source, and combinations thereof.

C1. A method of creating a database for use in identifying foreign material agricultural product that may be present in a manufacturing process for producing an agricultural product, the method utilizing hyperspectral imaging and comprising the steps of: (a) obtaining a dark image and a reference image for calibration; (b) analyzing the reference image to obtain calibration coefficients; (c) obtaining a hyperspectral image for an agricultural sample; (d) removing dark values and normalizing the agricultural sample image; (e) applying calibration coefficients to compensate for fluctuations in system operating conditions; (f) repeating steps (c)-(e) for all agricultural samples; (g) obtaining a hyperspectral image for a foreign material sample; (h) removing dark values and normalizing the agricultural sample image; (i) applying calibration coefficients to compensate for fluctuations in system operating conditions; (j) repeating steps (g)-(i) for all samples and (k) storing all hyperspectral sample hypercubes to form the database.

C2. A computer database stored in a computer readable medium, produced in accordance with the method of paragraph C1.

It is to be fully understood that certain aspects, characteristics, and features, of the forms disclosed herein, which are illustratively described and presented in the context or format of a plurality of separate forms, may also be illustratively described and presented in any suitable combination or sub-combination in the context or format of a single form. Conversely, various aspects, characteristics, and features, of the forms disclosed herein, which are illustratively described and presented in combination or sub-combination in the context or format of a single form, may also be illustratively described and presented in the context or format of a plurality of separate forms.

All patents, patent applications, and publications, cited or referred to in this specification are herein incorporated in their entirety by reference into the specification, to the same extent as if each individual patent, patent application, or publication, was specifically and individually indicated to be incorporated herein by reference. In addition, citation or identification of any reference in this specification shall not be construed or understood as an admission that such reference represents or corresponds to prior art. To the extent that section headings are used, they should not be construed as necessarily limiting.

While the forms disclosed herein have been described in connection with a number of exemplary forms, and implementations, the forms disclosed herein are not so limited, but rather cover various modifications, and equivalent arrangements, which fall within the purview of the present claims.

What is claimed:

1. A method for detecting foreign matter from an agricultural product stream of a manufacturing process, the method comprising:
   conveying a product stream past an inspection station;
   scanning a region of the conveyed product stream as the region of the conveyed product stream passes the inspection station using at least one light source;
   generating one or more hyperspectral images in real time from the scanned region;
   determining a product fingerprint from the one or more hyperspectral images in real time;
   comparing the product fingerprint in real time to a hyperspectral fingerprint database containing a plurality of hyperspectral fingerprints using a computer processor; and
   determining whether foreign matter is present based on the comparing the product fingerprint in real time to the hyperspectral fingerprint database.

2. The method of claim 1, further comprising:
   causing a portion of the conveyed product stream to fall under the influence of gravity in a cascade.

3. The method of claim 2, wherein the cascade is a turbulent cascade.

4. The method of claim 1, further comprising:
   removing a portion of the conveyed product stream in response to a determination that foreign matter is present.

5. The method of claim 4, wherein the removing the portion of the conveyed product stream includes directing fluid under pressure at the portion of the conveyed product stream.

6. The method of claim 5, wherein the fluid is a gas.

7. The method of claim 6, wherein the gas is pressurized air.

8. The method of claim 1, wherein the agricultural product is tobacco.

9. The method of claim 1, wherein the agricultural product is tea.

10. The method of claim 1, wherein the at least one light source is positioned to reduce an angle of incidence of each beam of light with the conveyed product stream.

11. The method of claim 1, wherein the at least one light source includes a tungsten light source, a halogen light source, a xenon light source, a mercury light source, an ultraviolet light source, or any combination thereof.

12. The method of claim 1, wherein the foreign matter is an oil or a lubricant.

13. A system for detecting foreign matter within an agricultural product stream, comprising:
   an inspection station including,
      at least one light source configured to provide a beam of light to scan a region of a product stream as it passes the inspection station, and
      a hyperspectral camera system configured to provide a three dimensional hyperspectral image cube from the scanned region in real time; and
   a computer processor configured to determine a product fingerprint from the hyperspectral image cube and to compare in real time the product fingerprint to a hyperspectral fingerprint database containing a plurality of hyperspectral fingerprints to determine whether foreign matter is present.

14. The system of claim 13, further comprising:
   at least one deflecting system responsive to signals obtained from said computer processor, the at least one deflecting system configured to remove a portion of the product stream in response to a determination of the computer processor that foreign matter is present in the product stream.

15. The system of claim 13, further comprising:
   at least one deflecting system responsive to signals obtained from the computer processor, the at least one deflecting system configured to direct fluid under pressure at a portion of the product stream in response to a determination of the computer processor that foreign matter is present in the product stream.

16. The system of claim 15, wherein the fluid so directed is effective to remove the foreign matter.

17. The system of claim 15, wherein the fluid is a gas.

18. The system of claim 17, wherein the gas is air.

19. The system of claim 13, wherein the agricultural product is tobacco.

20. The system of claim 13, wherein the agricultural product is tea.

21. The system of claim 13, wherein the at least one light source is positioned to reduce an angle of incidence of each beam of light with the conveyed product stream.

22. The system of claim 13, wherein the at least one light source includes a tungsten light source, a halogen light source, a xenon light source, a mercury light source, an ultraviolet light source, or any combination thereof.

23. The system of claim 13, wherein the foreign matter is an oil or a lubricant.

* * * * *